United States Patent
Oyola et al.

(10) Patent No.: US 9,359,320 B2
(45) Date of Patent: Jun. 7, 2016

(54) ACID-FUNCTIONALIZED POLYOLEFIN MATERIALS AND THEIR USE IN ACID-PROMOTED CHEMICAL REACTIONS

(71) Applicants: UT-Battelle, LLC, Oak Ridge, TN (US); University of Tennessee Research Foundation, Knoxville, TN (US)

(72) Inventors: Yatsandra Oyola, Paducah, KY (US); Chengcheng Tian, Shanghai (CN); John Christopher Bauer, Paducah, KY (US); Sheng Dai, Knoxville, TN (US)

(73) Assignees: UT-BATTELLE, LLC, Oak Ridge, TN (US); UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 78 days.

(21) Appl. No.: 14/032,727

(22) Filed: Sep. 20, 2013

(65) Prior Publication Data

US 2015/0087848 A1 Mar. 26, 2015

(51) Int. Cl.
  *C07D 307/48* (2006.01)

(52) U.S. Cl.
  CPC .................................. *C07D 307/48* (2013.01)

(58) Field of Classification Search
  CPC .................................................... C07D 307/48
  USPC ......................................................... 549/488
  See application file for complete search history.

(56) References Cited

U.S. PATENT DOCUMENTS

| | | | |
|---|---|---|---|
| 3,489,699 A * | 1/1970 | Battaerd et al. | 521/28 |
| 4,622,366 A | 11/1986 | Sugo et al. | |
| 7,572,925 B2 | 8/2009 | Dumesic et al. | |
| 2008/0230471 A1 | 9/2008 | Tamada et al. | |
| 2013/0071659 A1 | 3/2013 | Janke et al. | |

OTHER PUBLICATIONS

Mohammadi, A., "A novel polymeric catalyst for the one-pot synthesis of 2, 4, 5-triaryl-1 H-imidazoles." Journal of Chemical Sciences 124.3 (2012): 717-722.*

Takeuchi, T.,"Atrazine transformation using synthetic enzymes prepared by molecular imprinting." Organic & biomolecular chemistry 2.18 (2004): 2563-2566.*

Lee, S. W.,"Synthesis of a cation-exchange fabric with sulfonate groups by radiation-induced graft copolymerization from binary monomer mixtures." Reactive and Functional Polymers 68.2 (2008): 474-482.*

Rohm and Haas, Amberlyst-15 Wet Strongly Acidic Catalyst for Catalysis and Separation Technologies, Specification Sheet, 2003p. 1-4.*

Shimizu, K., "Enhanced production of hydroxymethylfurfural from fructose with solid acid catalysts by simple water removal methods." Catalysis Communications 10.14 (2009): 1849-1853.*

Al-Haq N. et al., "Oxidation of Alcohols Using Cerium(IV) Alkyl Phosphonate Modified Silica", Tetrahedron Letters 44:769-771 (2003).

Bugrayev A. et al., "Covalently Linked Ethylnnercaptophenyl Sulfonic Acid and Ethylmercaptobenzyl Sulfonic Acid Silica Materials-Synthesis and Catalytic Activity", Journal of Molecular Catalysis A: Chemical 280:96-101 (2008).

Deng T. et al., "Conversion of Carbohydrates into 5-Hydroxymethylfurfural Catalyzed by ZnCI2 in Water", Chemical Communications 48:5494-5496 (2012).

Jung E.J. et al., "Environmentally Benign, One-Pot Synthesis of Pyrans by Domino Knoevenagel/6π - Electrocyclization in Water and Application to Natural Products", Green Chem. 12:2003-2011 (2010).

Jurado-Gonzalez M. et al., "Allylic and Benzylic Oxidation Using Cobalt(II) Alkyl Phosphonate Modified Silica", Tetrahedron Letters 44:4283-4286 (2003).

Jurado-Gonzalez M. et al., "A New Solid Acid Catalyst: The First Phosphonate and Phosphonic Acid Functionalised Microporous Polysilsesquioxanes", Chemical Communications, Issue 1, pp. 67-68 (2001).

Kawai T. et al., "Preparation of Hydrophilic Amidoxime Fibers by Congrafting Acrylonitrile and Methacrylic Acid from an Optimized Monomer Composition", Radiation Physics and Chemistry 59:405-411 (2000).

Nakajima K. et al., "Nb2O5 nH2O as a Heterogeneous Catalyst With Water-Tolerant Lewis Acid Sites", Journal of the American Chemical Society 133:4224-4227 (2011).

Okayasu T. et al., "Poly(Vinylsulfonic Acid)-Grafted Solid Catalysts: New Materials for Acid-Catalysed Organic Synthetic Reactions", Green Chem. 12:1981-1989 (2010).

Okayasu T. et al., "Preparation of a Novel Poly(Vinylsulfonic Acid)-Grafted Solid Phase Acid Catalyst and its Use in Esterification Reactions", Chemical Communications Issue 31, pp. 4708-4710 (2009).

Shelly K.P., "General Acid and General Base Catalysis of the Enolization of Acetone. An Extensive Study", The University of British Columbia, Thesis (May 1988).

Tian C. et al., "A Recyclable SO3/PO3-Polyethylene Grafted Fiber Catalyst: An Efficient Heterogeneous Catalyst for the Synthesis of 5-Hydroxymethylfurfural from Fructose in Water", Oak Ridge National Laboratory, Oak Ridge, TN, 5 pages. (3052b).

Yin P. et al., "Production of Biodiesel by Esterification of Oleic Acid With Ethanol Over Organophosphonic Acid-Functionalized Silica", Bioresource Technology 110:258-263 (2012).

* cited by examiner

*Primary Examiner* — Samantha Shterengarts
*Assistant Examiner* — Matt Mauro
(74) *Attorney, Agent, or Firm* — Scully, Scott, Murphy & Presser, P.C.

(57) ABSTRACT

An acid-functionalized polyolefin material that can be used as an acid catalyst in a wide range of acid-promoted chemical reactions, wherein the acid-functionalized polyolefin material includes a polyolefin backbone on which acid groups are appended. Also described is a method for the preparation of the acid catalyst in which a precursor polyolefin is subjected to ionizing radiation (e.g., electron beam irradiation) of sufficient power and the irradiated precursor polyolefin reacted with at least one vinyl monomer having an acid group thereon. Further described is a method for conducting an acid-promoted chemical reaction, wherein an acid-reactive organic precursor is contacted in liquid form with a solid heterogeneous acid catalyst comprising a polyolefin backbone of at least 1 micron in one dimension and having carboxylic acid groups and either sulfonic acid or phosphonic acid groups appended thereto.

20 Claims, 6 Drawing Sheets

ACID-FUNCTIONALIZED POLYOLEFIN MATERIALS AND THEIR USE IN ACID-PROMOTED CHEMICAL REACTIONS

This invention was made with government support under Prime Contract No. DE-AC05-00OR22725 awarded by the U.S. Department of Energy. The government has certain rights in the invention.

FIELD OF THE INVENTION

The present invention relates to the field of acid catalysts for acid-promoted chemical reactions, and more particularly, to such catalysts in solid or heterogeneous form.

BACKGROUND OF THE INVENTION

Acid catalysts have found widespread use in the conversion of numerous organic chemical species to various end products. The organic chemical reaction in which the acid is used may be, for example, a dehydration, esterification, etherification, aldol condensation, enolization, oxidation, dehydrogenation, acetalization, or alkene hydration reaction. Typical acids include sulfuric, carboxylic, and phosphoric acids, particularly when a polar solvent is used. For non-polar solvents, the sulfonic acids (e.g., methanesulfonic acid and p-toluene sulfonic acid) are typically used.

Unfortunately, the wastes generated from these acid catalysts are environmentally harmful, and thus, require substantial time and cost in their removal, conversion to salt species, and storage as waste. Moreover, after conversion, the acids generally cannot be recovered in suitable form for further chemical reactions.

For this reason, efforts have been made in finding alternative acid catalysts having fewer drawbacks. For example, silica-based acid-functionalized catalysts have been used. However, the silica acid catalysts generally require filtration for their removal, as well as use of organic solvents, both of which result in significant labor, cost, and waste management.

SUMMARY OF THE INVENTION

In one aspect, the invention is directed to an acid-functionalized polyolefin material that can be used as an acid catalyst in a wide range of acid-promoted chemical reactions. The acid-functionalized polyolefin material includes a polyolefin backbone on which acid groups are appended. In particular embodiments, the appended acid groups are in the form of grafts containing a polyolefinic structure on which acid functional groups are attached. The acid functional groups can be selected from, for example, sulfonic, phosphonic, and carboxylic acid groups. In particular embodiments, the graft has the following chemical formula:

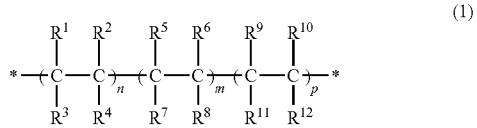

(1)

In Formula (1), $R^1$, $R^2$, $R^3$, $R^4$, $R^5$, $R^6$, $R^7$, $R^8$, $R^9$, $R^{10}$, $R^{11}$, and $R^{12}$ are independently selected from hydrogen atom, hydrocarbon groups R having at least 1 and up to 6 carbon atoms, acid groups (e.g., sulfonic acid, phosphonic acid, and/or carboxylic acid groups), halide, and non-acidic (neutral) hydrophilic groups containing at least one heteroatom selected from nitrogen, oxygen, sulfur, and phosphorus, provided that at least one of $R^1$, $R^2$, $R^3$, $R^4$, $R^5$, $R^6$, $R^7$, $R^8$, $R^9$, $R^{10}$, $R^{11}$, and $R^{12}$ is an acid group and/or acid precursor group or a hydrocarbon group substituted with at least one acid group and/or acid precursor group, and provided that the non-acidic hydrophilic group is not a basic group capable of neutralizing an acid group on the acid-functionalized polyolefin. The subscripts n, m, and p are independently selected from 0 and integers of at least 1, provided that the sum of n, m, and p is an integer of at least 2. In particular embodiments, at least one of $R^1$, $R^2$, $R^3$, $R^4$, $R^5$, $R^6$, $R^7$, $R^8$, $R^9$, $R^{10}$, $R^{11}$, and $R^{12}$ is a sulfonic acid or phosphonic acid group, and at least one of $R^1$, $R^2$, $R^3$, $R^4$, $R^5$, $R^6$, $R^7$, $R^8$, $R^9$, $R^{10}$, $R^{11}$, and $R^{12}$ is a carboxylic acid group.

In another aspect, the invention is directed to a method for fabricating the above-described acid-functionalized polyolefin material. In the method, a precursor polyolefin is subjected to ionizing radiation (for example, electron beam irradiation) of sufficient power and the irradiated precursor polyolefin reacted with at least one vinyl monomer, optionally in the presence of an initiator and/or solvent, to result in grafting and polymerization of the vinyl monomer onto the surface of the precursor polyolefin to produce the acid-functionalized polyolefin material or an acid precursor form thereof. At least a portion of the vinyl monomer contains one or more acid groups and/or groups that can be converted to acid groups (i.e., acid precursor groups). In particular embodiments, the vinyl monomer (which may be a single vinyl monomer or a mixture of different vinyl monomers) has the following chemical formula:

(2)

In Formula (2) above, $R^{13}$, $R^{14}$, $R^{15}$, and $R^{16}$ are independently selected from hydrogen atom, hydrocarbon groups R having at least 1 and up to 6 carbon atoms, acid groups (e.g., sulfonic acid, phosphonic acid, and/or carboxylic acid groups, or a hydrocarbon group containing one or more acid groups), acid precursor groups (e.g., nitrile-containing group), halide, and non-acidic (neutral) hydrophilic groups containing at least one heteroatom selected from nitrogen, oxygen, sulfur, and phosphorus, provided that at least one of $R^{13}$, $R^{14}$, $R^{15}$, and $R^{16}$ is an acid group and/or acid precursor group or a hydrocarbon group substituted with at least one acid group and/or acid precursor group, and provided that the non-acidic hydrophilic group is not a basic group capable of neutralizing an acid group on the acid-functionalized polyolefin. In some embodiments, a first portion of a mixture of vinyl monomers selects at least one of $R^{13}$, $R^{14}$, $R^{15}$, and $R^{16}$ as a sulfonic- or phosphonic-containing group (or precursor thereof, such as a sulfonate or phosphonate salt) and a second portion of the mixture of vinyl monomers selects at least one of $R^{13}$, $R^{14}$, $R^{15}$, and $R^{16}$ as a carboxylic-containing group or precursor thereof (e.g., nitrile-containing group).

In another aspect, the invention is directed to a method for conducting an acid-promoted chemical reaction by contacting an acid-reactive organic precursor under suitable reaction conditions with the acid-functionalized polyolefin catalyst described above in solid (i.e., heterogeneous) form. The solid heterogeneous catalyst can be, for example, a polyolefin macroscopic object of at least 1 micron in one dimension, wherein surfaces of the polyolefin macroscopic object have carboxylic acid groups and either sulfonic acid or phosphonic acid groups appended thereto. In particular embodiments, the acid-promoted reaction is conducted in an aqueous solution, which may contain only water as a solvent or water in admixture with a water-soluble solvent (e.g., an alcohol).

The acid-functionalized polyolefin catalysts described herein advantageously possess a level of activity substantially comparable to or even superior to acid catalysts of the art while being of lower cost by virtue of the inexpensive polyolefin raw materials. The resulting catalyst can furthermore be made to be substantially hydrophilic by incorporation of auxiliary hydrophilic groups (which may be acidic or non-acidic) to the extent that the acid-promoted reaction can advantageously be conducted in a solvent substantially or completely composed of water. As a further advantage, the catalyst described herein can be produced in non-particulate form (e.g., as fibers or other macroscopic object), thereby minimizing the labor and cost associated with removing the catalyst from the reaction medium and its separation from the product. In particular embodiments, the catalyst is in the form of a monolith (i.e., a single polyolefin macroscopic object, such as a mesh, sponge, foam, or fabric), thus advantageously permitting facile and quick removal of the catalyst from the reaction medium without the need for filtration or other separation process.

BRIEF DESCRIPTION OF THE DRAWINGS

FIG. 4A: Graph showing the effect of reaction time on fructose yield. FIG. 4B: Graph showing the effect of reaction time on fructose conversion to HMF at 120° C. FIG. 4C: Graph showing catalytic activity of reused acid-functionalized fibers ($H_2PO_3$-fiber, left bar of each pair; $HSO_3$-fiber, right bar of each pair) for HMF production from fructose at 120° C. for 6 hours.

DETAILED DESCRIPTION OF THE INVENTION

Figure 1:
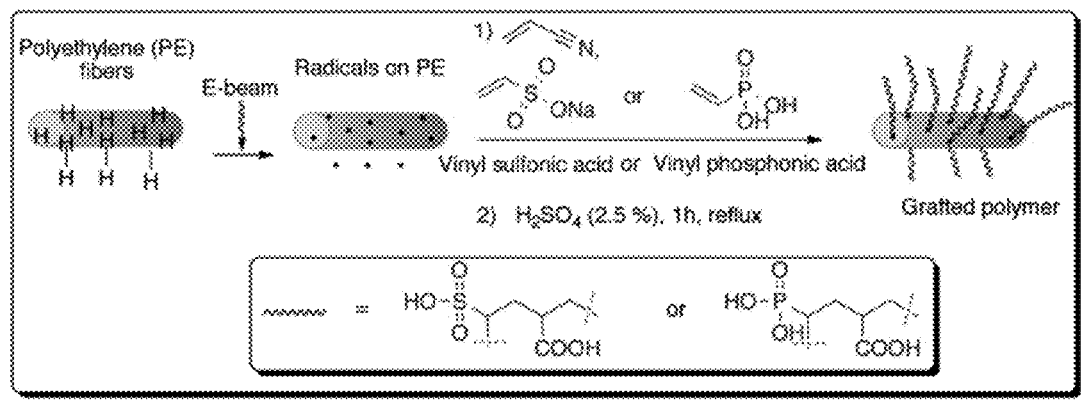
FIG. 1. Schematic showing a general procedure for the preparation of an $SO_3/PO_3$-polyethylene grafted fiber catalyst by a random co-polymerization of acrylonitrile and vinylsulfonic acid or vinylphosphonic acid, followed by hydrolysis of acrylonitrile.

As used herein, the term "about" generally indicates within ±0.5%, 1%, 2%, 5%, or up to ±10% of the indicated value. For example, a size of "about 10 μm" generally indicates in its broadest sense 10 μm±10%, which indicates 9.0-11.0 μm. Alternatively, the term "about" can indicate a variation or average in a physical characteristic of a group, e.g., a variation of sizes.

The term "hydrocarbon group" or "hydrocarbon linker" (also identified as "R"), as used herein, designates, in a first embodiment, groups or linkers composed solely of carbon and hydrogen and containing at least one carbon-hydrogen bond. In different embodiments, one or more of the hydrocarbon groups or linkers can contain precisely, or a minimum of (i.e., at least or above), or a maximum of (i.e., up to or less than), for example, one, two, three, four, five, six, seven, eight, nine, ten, eleven, or twelve carbon atoms, or a number of carbon atoms within a particular range bounded by any two of the foregoing carbon numbers. Hydrocarbon groups or linkers in different compositions described herein, or in different positions of a composition, may possess the same or different number (or preferred range thereof) of carbon atoms in order to independently adjust or optimize the activity or other characteristics of the composition.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene linker, i.e., —$CH_2$—, or methine linker), ethyl (or ethylene or dimethylene linker, i.e., —$CH_2CH_2$— linker), n-propyl, n-butyl, n-pentyl, n-hexyl, n-heptyl, n-octyl, n-nonyl, n-decyl, n-undecyl, and n-dodecyl groups (or their respective linker analogs).

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, and 3-methylpentyl. Some examples of branched alkylene linkers are those derived by removal of a hydrogen atom from one of the foregoing exemplary branched alkyl groups (e.g., isopropylene, —$CH(CH_3)CH_2$—).

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, and propargyl (2-propynyl). Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers can alternatively be unsaturated and branched (i.e., branched olefinic or alkenyl groups or linkers). Some examples of branched olefinic groups include propen-2-yl, 3-buten-2-yl ($CH_2$=CH—CH.—$CH_3$), 3-buten-3-yl ($CH_2$=C.—$CH_2$—$CH_3$), 4-penten-2-yl, 4-penten-3-yl, 3-penten-2-yl, 3-penten-3-yl, and 2,4-pentadien-3-yl. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers may also be substituted with one or more heteroatoms (i.e., non-carbon and non-hydrogen atoms), such as one or more heteroatoms selected from oxygen, sulfur, silicon, phosphorus, boron, and halide atoms, as well as heteroatom-containing groups that contain one or more of these heteroatoms (i.e., heteroatom-containing groups). Some examples of oxygen-containing groups include hydroxy (OH), alkoxy (OR), carbonyl-containing (e.g., carboxylic acid, ketone, aldehyde, carboxylic ester, amide, and urea functionalities), nitro ($NO_2$), carbon-oxygen-carbon (ether), sulfonyl, and sulfinyl (i.e., sulfoxide) groups. The ether group can also be a polyalkyleneoxide group, such as a polyethyleneoxide group. Some particular examples of alkoxy groups —OR include methoxy, ethoxy, n-propoxy, isopropoxy, n-butoxy, isobutoxy, t-butoxy, phenoxy, benzyloxy, 2-hydroxyethoxy, 2-methoxyethoxy, 2-ethoxyethoxy, vinyloxy, and allyloxy groups. Some examples of phosphorus-containing groups include —P(=O)$R_2$, —P(OR)$_2$, —O—P(OR)$_2$, —R—P(OR)$_2$, —P(=O)(OR)$_2$, —O—P(=O)(OR)$_2$, —O—P(=O)(OR)(R), —O—P(=O)$R_2$, —R—P(=O)(OR)$_2$, —R—P(=O)(OR)(R), and —R—P(=O)$R_2$ groups, wherein R is independently selected from hydrogen atom and hydrocarbon groups set forth above. Some examples of sulfur-containing groups include mercapto (i.e., —SH), thioether (i.e., sulfide, e.g., —SR), disulfide (—R—S—S—R), sulfoxide (—S(O)R), sulfone (—$SO_2$R), sulfonate (—S(=O)$_2$OR, wherein R is H, a hydrocarbon group, or a cationic group), and sulfate groups (—OS(=O)$_2$OR, wherein R is H, a hydrocarbon group, or a cationic group). Some examples of halide atoms include fluorine, chlorine, bromine, and iodine. One or more of the heteroatoms described above (e.g., oxygen, nitrogen, and/or sulfur atoms) can be inserted (i.e., as a linker) between carbon atoms (e.g., as —O— or —S—) in any of the hydrocarbon groups described above to form a heteroatom-substituted hydrocarbon group or linker. Alternatively, or in addition, one or more of heteroatom-containing groups, such as described above, can replace one or more hydrogen atoms on the hydrocarbon group or hydrocarbon linker.

In embodiments where the hydrocarbon group is or includes a cyclic group, the cyclic group may be, for example, monocyclic by containing a single ring without connection or fusion to another ring. The cyclic hydrocarbon group may alternatively be, for example, bicyclic, tricyclic, tetracyclic, or a higher polycyclic ring system by having at least two rings interconnected (i.e., by a bond) and/or fused.

In some embodiments, the cyclic hydrocarbon group is carbocyclic, i.e., does not contain ring heteroatoms (i.e., only ring carbon atoms). In different embodiments, ring carbon atoms in the carbocyclic group are all saturated, or a portion of the ring carbon atoms are unsaturated, or the ring carbon atoms are all unsaturated, as found in aromatic carbocyclic groups, which may be monocyclic, bicyclic, tricylic, or higher polycyclic aromatic groups.

In some embodiments, the hydrocarbon group is or includes a cyclic or polycyclic group that includes at least one ring heteroatom (for example, one, two, three, four, or higher number of heteroatoms). Such ring heteroatom-substituted cyclic groups are referred to herein as "heterocyclic groups". As used herein, a "ring heteroatom" is an atom other than carbon and hydrogen (typically, selected from nitrogen, oxygen, and sulfur) that is inserted into, or replaces a ring carbon atom in a hydrocarbon ring structure. In some embodiments, the heterocyclic group is saturated, while in other embodiments, the heterocyclic group is unsaturated (i.e., aliphatic or aromatic heterocyclic groups, wherein the aromatic heterocyclic group is also referred to herein as a "heteroaromatic ring" or a "heteroaromatic fused-ring system" in the case of at least two fused rings, at least one of which contains at least one ring heteroatom). In some embodiments, the heterocyclic group is bound via one of its ring carbon atoms to another group (i.e., other than hydrogen atom and adjacent ring atoms), while the one or more ring heteroatoms are not bound to another group. In other embodiments, the heterocyclic group is bound via one of its heteroatoms to another group, while ring carbon atoms may or may not be bound to another group.

Some examples of saturated heterocyclic groups include those containing at least one oxygen atom (e.g., oxetane, tetrahydrofuran, tetrahydropyran, 1,4-dioxane, 1,3-dioxane, and 1,3-dioxepane rings), or those containing at least one sulfur atom (e.g., tetrahydrothiophene, tetrahydrothiopyran, 1,4-dithiane, 1,3-dithiane, and 1,3-dithiolane rings), or those containing at least one oxygen atom and at least one sulfur atom (e.g., 1,4-thioxane). Some examples of unsaturated heterocyclic groups include those containing at least one oxygen atom (e.g., furan, pyran, 1,4-dioxin, and dibenzodioxin rings), or those containing at least one sulfur atom (e.g., thiophene, thianaphthene, and benzothiophene rings).

As used herein, the term "heteroatom-containing group" refers to any group that contains at least one heteroatom. In one embodiment, the heteroatom-containing group does not include a hydrocarbon portion (i.e., no portion that includes at least one carbon-hydrogen bond). Some examples of such heteroatom-containing groups include —OH, —SH, —O—, —S—, —C(O)OH, —C(S)OH, —C(O)H, —$NO_2$, —$SO_3$H, —$OSO_3$H, —Si(OCH$_3$)$_3$, —Si(OH)$_3$, —$SiR_2$—O—, —$PO_3$H, and —$OPO_3$H. In another embodiment, the heteroatom-containing group includes a hydrocarbon portion, e.g., —OCH$_3$, —OCH$_2$CH$_3$, —OCH(CH$_3$)$_2$, —SCH$_3$, —SCH$_2$CH$_3$, —SCH(CH$_3$)$_2$, —CH$_2$CH$_2$OCH$_2$CH$_3$, and —OCH$_2$CH$_2$OCH$_2$OCH$_2$CH$_3$.

Any of the generic forms or specific types of heteroatom-containing groups described above may function as any of the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ further described below. Alternatively, any one or more of the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ may be a hydrocarbon group (R) substituted one or more times with any of the foregoing heteroatom-containing functional groups.

In one aspect, the invention is directed to an acid-functionalized polyolefin material that can be used as a solid heterogeneous acid catalyst in a wide range of acid-promoted chemical reactions. The acid-functionalized polyolefin material includes a polyolefin backbone on which acid groups are appended (i.e., covalently attached), typically as polyvinyl polymer grafts containing acid groups. Both the polyolefin backbone and the polyvinyl polymer grafts appended thereto are polymeric units derived from polymerization (typically, addition polymerization) of vinylic monomer units, as further described below. Both the polyolefin backbone and polyvinyl polymer grafts typically contain only saturated carbon-carbon bonds in the polymer backbone; however, the polyolefin backbone and/or the polyvinyl polymer grafts may, in some instances, include carbon-carbon double bonds in the polymer backbone, as in polybutadiene.

Some examples of polyolefin backbone compositions include polyethylene, polypropylene, or a homogeneous or heterogeneous composite or mixture thereof, or a copolymer thereof. In the case of polyethylene, the polyethylene can be any of the types of polyethylene known in the art, e.g., low density polyethylene (LDPE), linear low density polyethylene (LLDPE), very low density polyethylene (VLDPE), high density polyethylene (HDPE), medium density polyethylene (MDPE), high molecular weight polyethylene (HMWPE), and ultra high molecular weight polyethylene (UHMWPE). In the case of polypropylene, the polypropylene can also be any of the types of polypropylenes known in the art, e.g., isotactic, atactic, and syndiotactic polypropylene. The polyolefin backbone may also be derived from, or include segments or monomeric units of other addition monomers, such as styrene, acrylic acid, methacrylic acid, acrylonitrile, and halogenated polyolefins (e.g., fluorinated, chlorinated, or brominated polyolefins) as found, for example, in polystyrene, polyacrylic acid, polyacrylonitrile, polyvinylfluoride, polyvinylidene fluoride, and polytetrafluoroethylene. Although the polyolefin backbone may be derived from any vinyl compound, including those that may include a silicon-containing or siloxane-containing group, in some embodiments, the polyolefin backbone and entire acid catalyst excludes silicon-containing or siloxane-containing groups, or the polyolefin backbone or entire acid catalyst is alternatively composed only of elements selected from C, H, N, O, S, and P. Ester groups (as found in methyl acrylate) and other acid-reactive groups are generally not included in the backbone or grafted portions (or in the precursor monomer) of the acid-functionalized polyolefin material, but may be included as acid precursor groups since their hydrolysis will generally yield carboxylic acid groups. In some embodiments, any one or more of the above polyolefin backbone types may be excluded.

In particular embodiments, the polyvinyl polymer grafts have the formula:

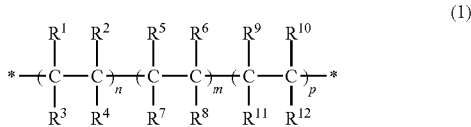

(1)

In Formula (1), $R^1$, $R^2$, $R^3$, $R^4$, $R^5$, $R^6$, $R^7$, $R^8$, $R^9$, $R^{10}$, $R^{11}$, and $R^{12}$ are independently selected from hydrogen atom, hydrocarbon groups R (typically, having at least 1 and up to 6 carbon atoms), acid groups (i.e., protonating or Brønsted acid groups, such as sulfonic acid, phosphonic acid, and/or carboxylic acid groups, or a hydrocarbon group containing one or more acid groups), acid precursor groups (e.g., nitrile-containing groups), halide (e.g., F, Cl, Br, or I), and non-acidic (neutral) hydrophilic groups containing at least one heteroatom selected from nitrogen, oxygen, sulfur, and phosphorus, provided that at least one of $R^1$, $R^2$, $R^3$, $R^4$, $R^5$, $R^6$, $R^7$, $R^8$, $R^9$, $R^{10}$, $R^{11}$, and $R^{12}$ is an acid group or a hydrocarbon group substituted with at least one acid group, and provided that the non-acidic hydrophilic group is not a basic group capable of neutralizing an acid group on the acid-functionalized polyolefin. The subscripts n, m, and p are independently selected from 0 or an integer of at least 1, provided that the sum of n, m, and p is an integer of at least 2. In particular embodiments, at least one of $R^1$, $R^2$, $R^3$, $R^4$, $R^5$, $R^6$, $R^7$, $R^8$, $R^9$, $R^{10}$, $R^{11}$, and $R^{12}$ is a sulfonic acid or phosphonic acid group, and at least one of $R^1$, $R^2$, $R^3$, $R^4$, $R^5$, $R^6$, $R^7$, $R^8$, $R^9$, $R^{10}$, $R^{11}$, and $R^{12}$ is a carboxylic acid group. A nitrile-containing group can be a nitrile group itself (i.e., cyano or —CN) or a hydrocarbon group R substituted with one, two, three, or more nitrile groups.

In some embodiments, the groups $R^1$, $R^2$, $R^3$, $R^4$, $R^5$, $R^6$, $R^7$, $R^8$, $R^9$, $R^{10}$, $R^{11}$, and $R^{12}$ are the same over all polymeric units n, m, and p. In other embodiments, one or more of the groups $R^1$, $R^2$, $R^3$, $R^4$, $R^5$, $R^6$, $R^7$, $R^8$, $R^9$, $R^{10}$, $R^{11}$, and $R^{12}$ may be different over polymeric units n, m, and p, in which case the polyvinyl polymer graft is copolymeric, such as a block, alternating, or random copolymer containing two, three, four, or higher number of distinct units. Moreover, Formula (1) can represent a portion (e.g., a block of a copolymer) or the entire polyvinyl polymer graft. By necessity, the composition depicted in Formula (1) has a terminating (capping) group, which may be any of the groups provided for groups $R^1$, $R^2$, $R^3$, $R^4$, $R^5$, $R^6$, $R^7$, $R^8$, $R^9$, $R^{10}$, $R^{11}$, and $R^{12}$.

In different embodiments, the sum of the subscripts n, m, and p is precisely, at least, above, or no more than 2, 3, 4, 5, 10, 12, 15, 18, 20, 25, 30, 35, 40, 45, or 50, or a particular range bounded by any two of the foregoing values. Moreover, each of the subscripts n, m, and p may independently be any of the foregoing values, wherein none of n, m, and p are zero, or one of n, m, and p is zero, or two of n, m, and p are zero.

The non-acidic hydrophilic group is any group that is less acidic than the acid groups present on the acid-functionalized polyolefin, and which is also non-basic to the extent that it is incapable of neutralizing (i.e., deprotonating) an acid group on the acid-functionalized polyolefin. Any heteroatom-containing group described above of sufficient hydrophilicity can be selected as a hydrophilic group. In one embodiment, one, two, three, or more of $R^1$, $R^2$, $R^3$, $R^4$, $R^5$, $R^6$, $R^7$, $R^8$, $R^9$, $R^{10}$, $R^{11}$, and $R^{12}$ may be selected from inorganic heteroatom-containing functional groups, such as hydroxy (OH), mercapto (SH), and nitro groups. In other embodiments, one, two, three, or more of $R^1$, $R^2$, $R^3$, $R^4$, $R^5$, $R^6$, $R^7$, $R^8$, $R^9$, $R^{10}$, $R^{11}$, and $R^{12}$ may be selected from organic heteroatom-containing functional groups, such as alkoxy (OR) and sulfide (SR) groups, wherein the group R is defined as above, except with up to two or three carbon atoms directly linked with each other, or may also be a hydrophilic heteroatom-containing chain, such as a hydroxyalkylene, dialkyleneoxy, trialkyleneoxy, or polyalkylene oxide (e.g., a polyethylene oxide).

In some embodiments, two of $R^1$, $R^2$, $R^3$, $R^4$, $R^5$, $R^6$, $R^7$, $R^8$, $R^9$, $R^{10}$, $R^{11}$, and $R^{12}$ (e.g., $R^2$ and $R^4$) can be crosslinked, either within a polymeric unit subtended by n, m, or p (as in polybutyral or polycyclopentene) or between polymeric units to form a cyclic group. In other embodiments, the polyinyl polymer graft shown in Formula (1) can include a level of unsaturation by including a carbon-carbon double bond between the shown carbon atoms, in which case two of $R^1$, $R^2$, $R^3$, $R^4$, $R^5$, $R^6$, $R^7$, $R^8$, $R^9$, $R^{10}$, $R^{11}$, and $R^{12}$ on adjacent carbon atoms are removed from the formula to form a double bond.

The acid-functionalized polyolefin described above can have any suitable shape or morphology, and any suitable size in the macroscopic range. The acid-functionalized polyolefin can be, for example, in the form of fibers, particles, or a porous object, such as a woven or non-woven fabric, sponge, mesh, or foam. The term "fiber" generally indicates a length dimension at least five times longer than a width dimension. The term "macroscopic" generally indicates a length of at least 1 micron for at least one dimension of the object. In different embodiments, one, two, or all three dimensions of the acid-functionalized polyolefin have lengths of at least 1, 2, 3, 4, 5, 10, 15, 20, 30, 40, 50, 60, 70, 80, 90, 100, 150, 200, 250, 300, 350, 400, 500, 1000, or 5000 microns (5 mm), or even 1, 2, 3, 4, 5, or 10 cm, or a size within a range bounded by any two of the foregoing values. In the case of a fiber, the fiber can have a length and width selected from any two of the foregoing values, e.g., a width of at least 1, 2, 5, 10, 15, 20, 30, 40, or 50 microns and a length of at least 10, 25, 50, 100, 500, or 1000 microns (1 mm), or 2, 5, or 10 mm, as long as the length is greater than the width.

In another aspect, the invention is directed to a method for fabricating the acid-functionalized polyolefin composition described above. In the method, a precursor polyolefin, which can have any of the compositions, shapes, and forms described above for the polyolefin backbone, is subjected to ionizing radiation of sufficient power, and the irradiated precursor polyolefin reacted with at least one vinyl monomer, optionally in the presence of an initiator and/or solvent, to result in grafting and polymerization of the vinyl monomer onto the surface of the precursor polyolefin to produce the acid-functionalized polyolefin material or an acid precursor form thereof. At least a portion of the vinyl monomer contains one or more acid groups and/or acid precursor groups (i.e., groups that can be converted to acid groups). The ionizing radiation can be, for example, gamma, electron beam, x-ray, or neutron irradiation. The radiative dose is typically at least 10, 20, 30, 40, or 50 kGy and up to 100, 200, 300, 400, or 500 kGy. The irradiating process is generally conducted in an inert atmosphere (e.g., nitrogen or argon) and the resulting irradiated polyolefin stored in the inert environment to preserve the free radicals prior to grafting. For example, the polymer fibers can be sealed within a nitrogen environment, optionally at subzero temperatures, to prevent oxygen from reacting with the newly formed free radicals. While irradiation is typically conducted separately from graft polymerization, exposure to ionizing radiation can alternatively occur in the presence of the grafting monomers in liquid or vapor form while under inert conditions. For example, the method of the present invention can include simultaneously irradiating a high surface area polymer fiber while in the presence of polymerizable monomers in liquid form.

In particular embodiments, the vinyl monomer (which hereinafter can refer to either a single vinyl monomer or a mixture of different vinyl monomers) has the following chemical formula:

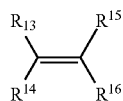

(2)

In Formula (2), $R^{13}$, $R^{14}$, $R^{15}$, and $R^{16}$ are independently selected from hydrogen atom, hydrocarbon groups R (typically, having at least 1 and up to 6 carbon atoms), acid groups (i.e., protonating or Brønsted acid groups, such as sulfonic acid, phosphonic acid, and/or carboxylic acid groups, or a hydrocarbon group containing one or more acid groups), acid precursor groups (e.g., nitrile-containing group), halide (e.g., F, Cl, Br, or I), and non-acidic (neutral) hydrophilic groups containing at least one heteroatom selected from nitrogen, oxygen, sulfur, and phosphorus, provided that at least one of $R^{13}$, $R^{14}$, $R^{15}$, and $R^{16}$ is an acid group and/or acid precursor group or a hydrocarbon group substituted with at least one acid group and/or acid precursor group, and provided that the non-acidic hydrophilic group is not a basic group capable of neutralizing an acid group on the acid-functionalized polyolefin. All of the general and specific embodiments provided for Formula (1) apply to Formula (2) herein.

In a first embodiment, a single vinyl monomer is used for reacting with the irradiated polyolefin, which results in homopolymeric grafts appended to the polyolefin backbone. In the latter case, the single vinyl monomer contains at least one of $R^{13}$, $R^{14}$, $R^{15}$, and $R^{16}$ that is an acid group and/or acid precursor group or a hydrocarbon group substituted with at least one acid group and/or acid precursor group. In a second embodiment, a mixture (i.e., two, three, four, or more types) of vinyl monomers is used for reacting with the irradiated polyolefin, which results in copolymeric grafts, typically of a random orientation, appended to the polyolefin backbone. In the latter case, at least one of the vinyl monomers (i.e., "first monomer") in the mixture contains at least one of $R^{13}$, $R^{14}$, $R^{15}$, and $R^{16}$ that is an acid group and/or acid precursor group or a hydrocarbon group substituted with at least one acid group and/or acid precursor group. Other vinyl monomers in the mixture may not have acidic groups, such as only hydrogen groups (i.e., ethylene), or one or more hydrocarbon groups (e.g., propylene or styrene), or one or more non-acidic hydrophilic groups (e.g., 2-hydroethylacrylate or allyl alcohol), or one or more acid precursor groups (e.g., acrylonitrile, methacrylonitrile, chloroacrylonitrile, vinylidene cyanide, tricyanoethylene, crotonitrile, pent-3-enenitrile, or 2-hydroxy-3-methylpent-3-enenitrile), or the other vinyl monomers in the mixture may have one or more acidic groups distinct from the acid groups on the first monomer. In particular embodiments, a first portion of a mixture of vinyl monomers selects at least one of $R^{13}$, $R^{14}$, $R^{15}$, and $R^{16}$ as a sulfonic- or phosphonic-containing group (or precursor thereof, such as a sulfonate or phosphonate salt) and a second portion of the mixture of vinyl monomers selects at least one of $R^{13}$, $R^{14}$, $R^{15}$, and $R^{16}$ as a carboxylic-containing group or precursor thereof (e.g., nitrile-containing group).

The above-described sonochemical grafting and polymerization process can typically achieve a degree of grafting (i.e., grafting yield) of at least 50%. In different embodiments, the grafting yield is at least 50, 60, 70, 80, 90, 100, 120, 150, 180, 200, 250, or 300%. The acid catalyst can have an acid density of at least 2, 3, 4, 5, 6, 6.5, 7, 7.5, or 8 mmol $H^+$/g.

In another aspect, the invention is directed to a method for conducting an acid-promoted chemical reaction by contacting an acid-reactive organic precursor (i.e., "precursor") in liquid form under suitable reaction conditions with the acid-functionalized polyolefin catalyst (i.e., "acid catalyst") described above in solid (i.e., heterogeneous or immobilized) form. The acid-reactive organic precursor can be any organic chemical compound or material that can be transformed into a useful product when reacted with the acid catalyst. The acid-promoted chemical reaction can be, for example, a dehydration, esterification, etherification, aldol condensation, enolization, oxidation, dehydrogenation, acetalization, or alkene hydration reaction, all of which are well-known in the art. In the case of esterification, the acid-catalyzed reaction may be, for example, the esterification of oleic acid with ethanol to form a biodiesel, or a pinacol-pinacolone rearrangement, particularly with use of a phosphonic acid-containing catalyst.

In one embodiment, the precursor is in liquid form by being in a liquid state in the absence of a solvent or liquifying agent under the reaction conditions (i.e., temperature and pressure) used in the reaction. The latter embodiment can be referred to as a reaction conducted in the "neat state", wherein the precursor can be in solid form at room temperature prior to the reaction but in a melted (neat) state during the reaction at an elevated temperature, or the precursor can be in liquid form at both room temperature and an elevated reaction temperature. In another embodiment, the precursor is in liquid form by being within a polar solvent. By being within a polar solvent, the precursor is generally fully dissolved in the polar solvent; however, in some cases, the precursor may not be fully dissolved (as in the case of a suspension or emulsion) or may be within a biphasic medium, which can include the polar solvent and an immiscible solvent in contact with each other. In a biphasic medium, the precursor may be partly or completely dissolved in either the polar solvent or immiscible (e.g., non-polar) solvent or both. In any event, whether the precursor is in the neat state or within a solvent, the acid catalyst is contacted with the precursor by being at least partially (i.e., partially or completely) immersed in the liquid form of the precursor. In some embodiments, to facilitate reaction efficiency, a flow mechanism is included, as provided by, for example, mechanical or magnetic stirring of the liquid medium, pump flowing of the liquid medium, spinning of the catalyst, or agitation of the liquid medium and/or acid catalyst.

The polar solvent included in the reaction medium can be a single polar solvent or a mixture of polar solvents, any of which may be protic or aprotic. A mixture of polar solvents can include two or more solvents, generally in a single phase. The solvent in contact with the acid catalyst should be non-reactive with the acid catalyst. Some examples of polar protic solvents include water, the alcohols (e.g., methanol, ethanol, isopropanol, or n-butanol), and diols (e.g., ethylene glycol, diethylene glycol, triethylene glycol). Some examples of polar aprotic solvents include the sulfoxides (e.g., dimethylsulfoxide, i.e., DMSO, or methyl sulfone, ethyl methyl sulfone, methyl phenyl sulfone, methyl isopropyl sulfone) and organochlorides (e.g., methylene chloride, chloroform, 1,1,-trichloroethane). In particular embodiments, the acid-promoted reaction is conducted in an aqueous solution, which contains either only water as a solvent or water in admixture with a water-soluble solvent (e.g., an alcohol).

Generally, the one or more polar solvents are non-reactive with the acid groups on the acid-functionalized polyolefin catalyst. Generally, ether solvents (e.g., diethyl ether or tetrahydrofuran), cyano-containing solvents (e.g., acetonitrile), amide-containing solvents (e.g., dimethylformamide and 2-pyrrolidone), and amine-containing and ester-containing solvents are unacceptably reactive with acids and can be excluded. Nevertheless, in some reactions, the polar solvent may participate in the acid-promoted reaction, e.g., in converting triphenylphosphine to triphenylphosphine oxide in DMSO, or oxidation of amino acids in the presence of DMSO.

In particular embodiments, the polar solvent is aqueous-based by being composed substantially or completely of water. The concentration of water in the aqueous-based solvent is generally at least 5 wt % (or vol %). In different embodiments, the concentration of water in the aqueous-based solvent is precisely, about, at least, above, up to, or less than, for example, 5, 10, 15, 20, 25, 30, 35, 40, 45, 50, 60, 70, 75, 80, 90, 95, 98, 99, or 100 wt % (or vol %). Thus, the aqueous-based solvent can be substantially or completely pure water (i.e., in the substantial or complete absence of a water-soluble or water-insoluble organic solvent), or may be a mixture of water and one or more water-soluble organic solvents, such as one or more alcohols, diols, sulfoxides, or other water-soluble solvents.

The liquid reaction medium may or may not include additional components besides the organic precursor and a polar solvent. The additional components can be any of those well known in the art, such as salts, buffering agents, pH adjusting agents, and surfactants.

In a first set of embodiments, the acid catalyst is in the form of a plurality of macroscopic objects, such as a plurality of fibers, chunks, particles, rods, or hollow tubules in the reaction vessel. In other embodiments, the acid catalyst is in the form of a single (i.e., monolithic) object in the reaction vessel, particularly a single porous object, such as a mesh, foam, sponge, or fabric. The latter embodiment is particularly advantageous in that the single catalyst object can be easily removed from (i.e., separated from) the reaction medium and precursor by a process not requiring filtration, such as simple lifting of the acid catalyst out of the liquid reaction contents, or draining of the liquid reaction contents. In some embodiments, the single catalyst object takes a significant volume of the reaction vessel, such as 10, 20, 30, 40, 50, 60, 70, 80, 90, or 100% of the volume of the reaction vessel during the reaction. Thus, in some embodiments, the acid catalyst can measure at least 1, 2, 5, 10, 20, or 30 cm from end to end, depending on the size of the reaction vessel.

After being used in a first acid-promoted reaction, the acid catalyst can advantageously be re-used in one or more subsequent acid-promoted reactions. For example, the acid catalyst may be used and re-used (i.e., in total) at least two, three, four, five, six, seven, or eight times at a temperature and reaction time of interest. In some embodiments, a yield of at least or above 10%, 12%, 15%, 18%, 20%, 25%, 30%, 35%, 40%, 45%, 50%, 60%, 70%, 80%, or 90% is maintained after the acid catalyst is re-used at least one, two, three, four, five, six, or seven times. If necessary, after completion of the first reaction, the acid catalyst is optionally cleaned and rinsed, and may also be regenerated, if necessary, by contact with a solution of a mild or strong acid.

The acid-promoted chemical reaction can employ any suitable temperature, pressure, and reaction time, well known in the art, for conducting such reactions. For example, depending on the reaction, the temperature may be conducted at room temperature (approximately 18-30° C. or 20-25° C.), a reduced temperature (e.g., −10, 0, or 10° C.), or an elevated temperature, such as 40, 50, 60, 70, 80, 90, 100, 120, 150, 180, or 200° C., or a temperature within a range bounded by any two of the foregoing temperatures, as long as the temperature is not high enough to melt or otherwise adversely affect the acid catalyst. For many reactions, the pressure is typically standard pressure, i.e., approximately 1 atm. However, some reactions may employ an elevated pressure (e.g., over 1 atm, such as 2, 5, 10, 20, or 50 atm) or a reduced pressure (e.g., less than 1 atm, such as 0.5 or 0.1 atm). Once the acid catalyst is removed, the product can be isolated and optionally purified according to methods well known in the art, such as extraction, distillation, crystallization, and re-crystallization.

An acid-promoted reaction of particular consideration herein is the dehydration reaction. In a dehydration reaction, an acid catalyst promotes the loss of water from a precursor, thereby converting the precursor to a dehydrated product. Some examples of dehydration reactions include the conversion of alcohols to ethers, the conversion of alcohols to alkenes, the conversion of amides to nitriles, and conversion of carboxylic acids to acid anhydrides. In particular embodiments, the dehydration reaction converts a hexose (e.g., fructose or glucose) into a furfural derivative, such as 5-hydroxymethylfurfural, (HMF) which is a known useful feedstock in the production of plastics and fine chemicals. In some embodiments, the HMF is further converted to 2,5-dimethylfuran, a liquid biofuel, by means well known in the art. The precursor hexose can be obtained commercially, or alternatively, derived from biomass by means well known in the art. By using the acid catalyst described herein, a solvent composed substantially or completely of water can advantageously be used. Moreover, the acid catalyst described herein may attain a yield of 5-HMF of at least 20%, 25%, 30%, 35%, 40%, 45%, or 50%, with a selectivity of at least 25%, 30%, 35%, 40%, 45%, 50%, 55%, 60%, 65%, or 70%. The acid catalyst may furthermore exhibit an at least 50%, 60%, 65%, 70%, 75%, 80%, 85%, or 90% conversion of fructose to HMF at 80, 90, 95, 100, 110, 120, 130, or 140° C. (or within a range therein) within the first 2, 3, 4, 5, 6, 7, 8, 9, 10, 11, or 12 hours, and/or an at least 85%, 90%, 95%, or nearly complete (e.g., 98-100%) conversion of fructose in the next 10, 15, 18, 20, 25, or 30 hours.

The acid catalyst described herein contains acid functional groups, which, in protonated form, are known to be poor or even ineffective as metal binders, adsorbers, or chelators. Thus, in particular embodiments, the method described herein excludes metal capturing (i.e., binding, adsorption, chelation, or complexation). Moreover, as the acid-functionalized polyolefin composition described herein is primarily directed to acid-promoted chemical reactions of organic precursors, certain embodiments exclude effective metal-capturing functional groups on the acid-functionalized polyolefin composition. Some examples of effective metal-capturing functional groups include carboxylates (i.e., deprotonated as salt form), amines, diamines, carboxamides, oximes, amidoximes, mercaptans, heterocyclic rings (e.g., pyridine or bipyridine), crown ethers, and cryptands, any or all of which may be excluded as functional groups in the acid-functionalized polyolefin composition, and many of which may also be improperly reactive with the acid groups. Moreover, in some embodiments, the method described herein excludes acid-functionalized silicon-containing or siloxane-containing compositions and/or free acids (e.g., sulfuric, sulfonic, phosphoric, phosphonic, nitric, carboxylic, or hydrohalogenic acids), or the method employs only the acid-functionalized polyolefin catalyst described herein as an acid catalyst.

Examples have been set forth below for the purpose of illustration and to describe certain specific embodiments of the invention. However, the scope of this invention is not to be in any way limited by the examples set forth herein.

EXAMPLES

Synthesis of 5-Hydroxymethylfurfural from Fructose in Water by Use of a Recyclable Heterogeneous $SO_3/PO_3$-Polyethylene Grafted Fiber Catalyst Overview Renewable biomass resources have the potential to reduce the demand on fossil fuels as a feedstock for the production of plastics and fine chemicals. In particular, furan derivatives, such as 5-hydroxymethylfurfural (HMF), have been identified as a key intermediate for the production of carbohydrate-derived chemical feedstocks, pharmaceuticals, and fuels. HMF can be obtained from renewable biomass resources by an acid-catalyzed dehydration of hexoses. Unfortunately, the high production cost of HMF limits its use on an industrial scale. To increase the yield of fructose to HMF, many catalysts have been explored, including liquid acids, solid acids (e.g., H-mordenites/zeolites), transition metal phosphates, protonated titanate nanotubes, and Lewis acids, such as metal chlorides and niobic acid. Although soluble acids are inexpensive and are highly active catalysts for dehydration reactions, solid acid catalysts are more desirable because they tend to be less corrosive, easier to separate, and more readily adapted to large-scale and continuous production. However, the known acidic heterogeneous catalysts tend to suffer from low conversion, selectivity, or both, depending on the solvent system used, particularly in the case of water. Moreover, although yields can be improved using high boiling point organic solvents, such as dimethylsulfoxide, these high boiling point solvents are generally expensive (compared to water and the simple alcohols) and toxic, thus generally requiring difficult and energy-intensive isolation procedures. Water, as an environmentally friendly and economical solvent, has become the most desirable choice for HMF preparation; however, the dehydration of fructose in aqueous media generally suffers from a low degree of selectivity, which leads to the formation of insoluble humins. As further discussed below, the acid catalyst described herein advantageously permits the dehydration of fructose to HMF in water while maintaining a significant degree of selectivity, and with lower cost and reduced energy demand.

Preparation of the Recyclable Heterogeneous $SO_3/PO$-Polyethylene Grafted Fiber Catalyst The catalyst fibers were synthesized by electron beam irradiation-induced co-grafting of acrylonitrile (subsequently hydrolyzed to carboxylic acid (—COOH) groups) and either vinylsulfonic acid ($CH_2$=CH—$SO_3H$) or vinylphosphonic acid ($CH_2$=CH—$PO_3H_2$) on a polyethylene (PE) fabric and subsequent hydrolysis of the nitriles by heating at 80° C. for 1 hour in a 2.5% sulfuric acid solution. A general summary of the process is provided in FIG. 1.

Figure 2:
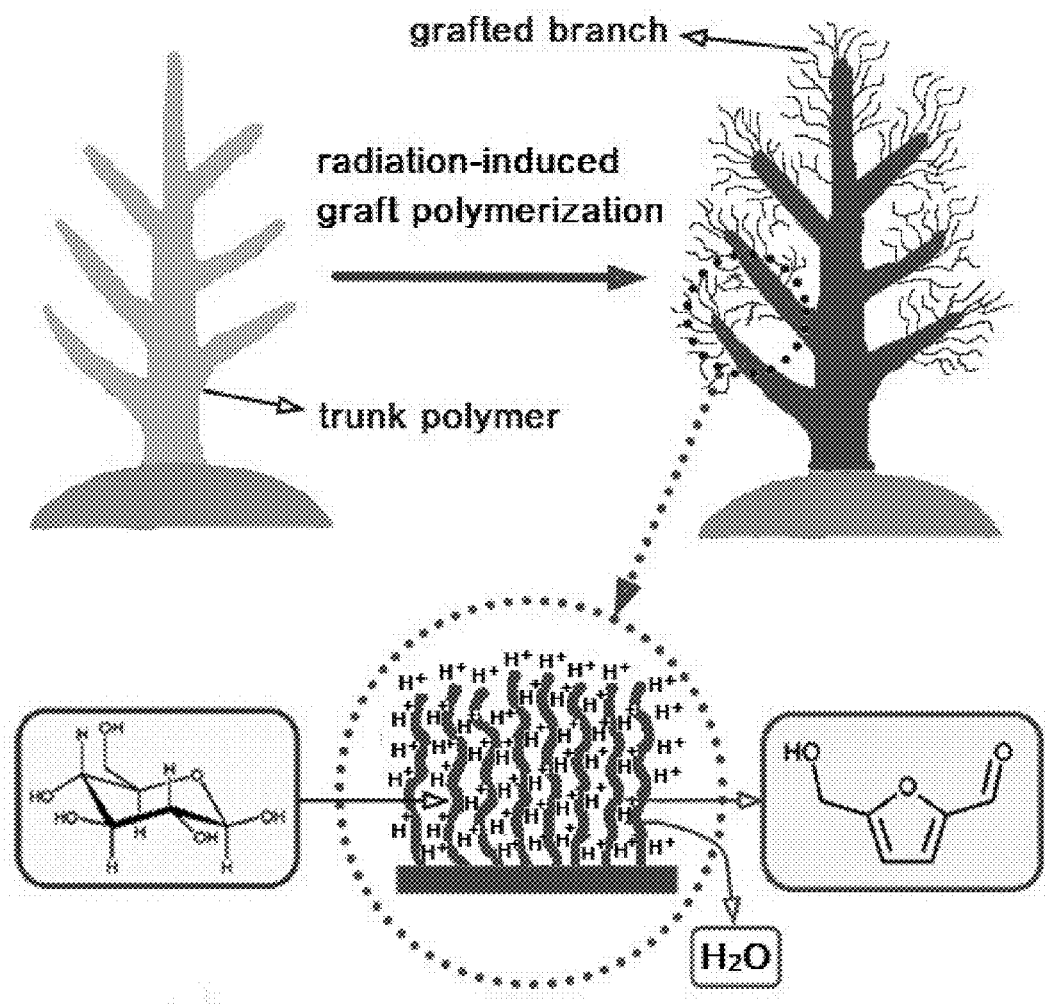
FIG. 2. Schematic showing the general process for the dehydration of fructose to HMF catalyzed by the grafted fiber catalyst depicted in FIG. 1.

As shown in FIG. 2, the exemplified catalyst consists of a polyethylene (PE) fiber trunk grafted with random co-polymerization of acrylonitrile and either vinyl sulfonic acid or vinyl phosphonic acid. As a result of the radiation-induced grafting process, an ultrahigh 157% or 280% degree of grafting was achieved for acrylonitrile mixed with either vinyl sulfonic acid or vinyl phosphonic acid co-monomers, respectively. The highly functionalized acidic polymer chains are covalently grafted to the PE fiber surface with a surface density as high as 0.4 chains/nm, thereby creating a unique micro-environment that provides a high catalytic activity for the dehydration of fructose.

The S/P composition of the grafted co-polymer onto the polyethylene was determined by elemental analysis, the results of which are provided in Table 1 below. Other characterization techniques concurred with the presence of carboxylic acid and sulfonic acid polymer or phosphonic acid copolymer in the fiber catalyst. The IR spectra of both grafted fiber samples show the band around 1735 $cm^{-1}$ assigned to the C=O stretching vibration of the COOH group compared to that of the PE fiber. Also, a residual band at 2250 $cm^{-1}$ appeared, indicating that some unconverted —CN was still present after the hydrolysis step. Two bands corresponding to the asymmetric stretching vibrational band at 1176 $cm^{-1}$ and symmetric stretching vibration band at 1040 $cm^{-1}$ of the O=S=O moiety were positively identified in the sulfonic acid co-grafted catalyst fiber ($HSO_3$-fiber). In the IR spectrum of the phosphonic acid co-grafted catalyst fiber ($H_2PO_3$-fiber) a band at 1226 $cm^{-1}$ and a band at 1186 $cm^{-1}$ were observed, corresponding to the P=O stretching vibrations. Additionally, the $^{31}P$ solid-state MAS NMR spectrum of the $H_2PO_3$-fiber showed a sharp peak in the region characteristic for phosphonic acid groups (27-34 ppm), in agreement with the presence of —$H_2PO_3$ in the fiber.

The measurement of the acid density by neutralization titration methods confirms the number of acid groups introduced onto the trunk fiber by the grafting polymerization. Table 1 presents the acid site density of the fiber catalysts used for the reaction. The acid densities for $HSO_3$-fiber and $H_2PO_3$-fiber were approximately 6.84 mmol $H^+/g$ and 6.25 mmol $H^+/g$, respectively. This level was much higher than those found as strong Brønsted acid sites in Nafion (0.9 mmol $H^+/g$) and Amberlyst-15 (4.8 mmol $H^+/g$). Even after the reaction of fructose dehydration, the fiber catalyst still exhibited a similar acid site density, indicating reusability.

TABLE 1

Surface and adsorption properties of the prepared catalysts and their catalytic performances

| catalyst | acid density$^a$ (mmol/g) | $R_1{}^b$ (mg/g) | $R_2{}^c$ (mg/g) | yield$^d$ (%) | selectivity$^d$ (%) | S$^e$ (%) | P$^e$ (%) |
| --- | --- | --- | --- | --- | --- | --- | --- |
| $HSO_3$-fiber | 6.84 | 134 | 0 | 34 | 47 | — | 0.24 |
| $H_2PO_3$-fiber | 6.25 | 100 | 0 | 27 | 34 | 0.20 | — |

$^a$Acidity calculated using the titration method
$^b$The adsorption quality of fructose per gram of catalyst
$^c$The adsorption quality of HMF per gram of catalyst
$^d$Yield and selectivity for HMF. Reaction conditions: fructose 6.5 wt %, catalyst 10 wt %, temperature (T) = 120° C., solvent is $H_2O$, for 6 hours
$^e$Sulfur (S) was determined by titration, and phosphorus was determined (P) by ICP.

Figure 3:
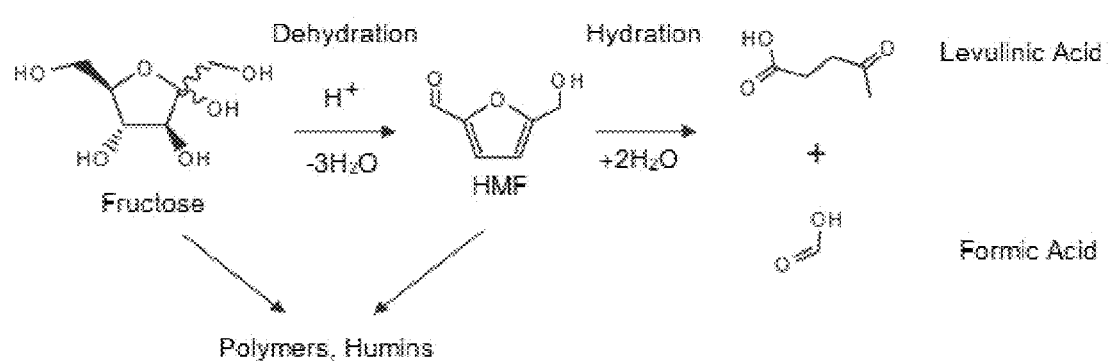
FIG. 3. Schematic showing the pathways involved in the fructose dehydration reaction to HMF and products of further HMF dehydration.

When the PE fibers are added to water they swell and the hydrophilic grafted chains interact very favorably with water. When fructose molecules travel near the fibers, they experience a highly concentrated microenvironment of the hydrated organic acid groups, leading to the catalytic formation of HMF molecules by the loss of three water molecules. This microenvironment is very different from the bulk aqueous phase and resembles the reaction environments created by two-phase catalytic systems. As shown by the scheme in FIG. 3, a subsequent hydration reaction consumes two water molecules to yield levulinic acid, while formic acid formation can be restrained, consequently leading to an increase in the selectivity and yield for HMF.

Dehydration of Fructose in Water to Produce 5-Hydroxymethylfurfural (HMF) Product The catalytic performance of the acid fiber catalyst was determined by applying it to the dehydration of fructose in water. The results show that this heterogeneous catalyst is highly efficient in terms of activity, selectivity, and reusability at mild conditions. After 6 hours, the yield of HMF was 34% and 27% for $HSO_3$-fiber and $H_2PO_3$-fiber, respectively, at 120° C. in water. These yields are generally improved as compared to some of the commonly available commercial solid acids, such as Nafion NR50 and Amberlyst-15 (<5%), and protonated titanate nanotubes (about 16%), under similar conditions. Even after recycling four times, the yield of HMF still remained at 30% and 21%.

Some advantages provided by the above-described co-polymer grafted PE fiber catalyst include ease of purification, higher conversion rates, improved selectivity toward HMF, and recyclability. In particular, although the co-polymers are hydrophilic, they are attached to a macroscopic hydrophobic PE trunk, which makes this heterogeneous catalyst very easy to remove from the reaction without the need for special extraction techniques or fine filtration. Furthermore, no expensive or toxic organic solvents are required and as a result, HMF does not have to be purified, all of which dramatically reduces cost.

Figure 4A:
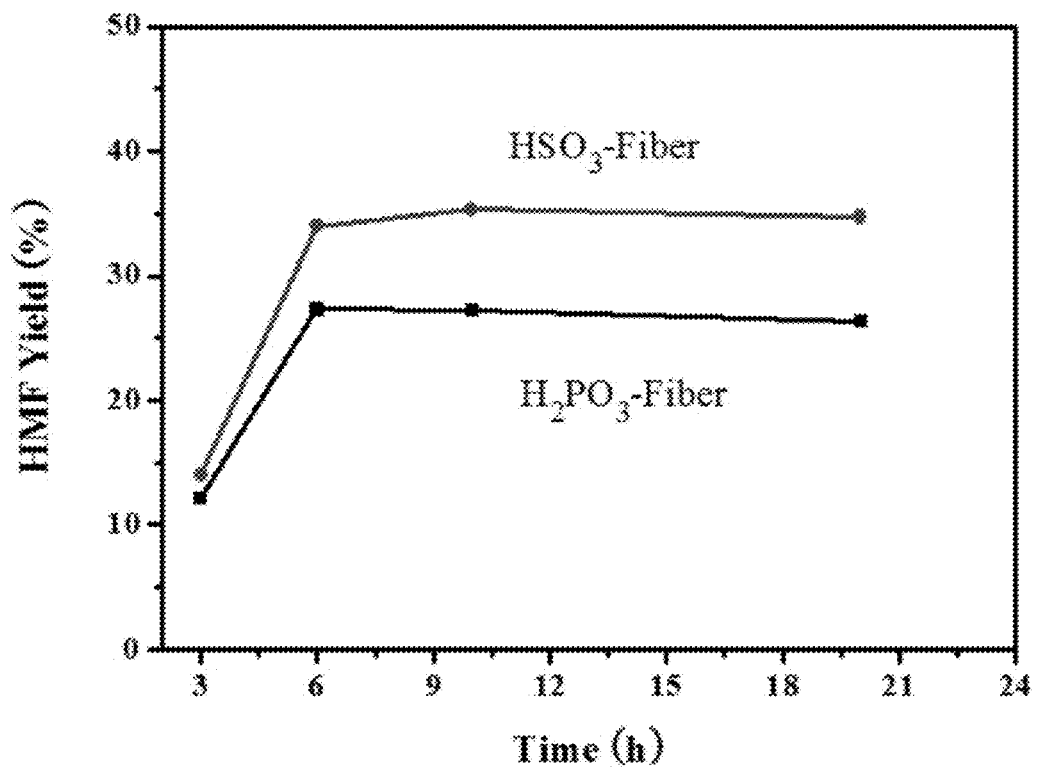
FIGS. 4A-4C.
Figure 4B:
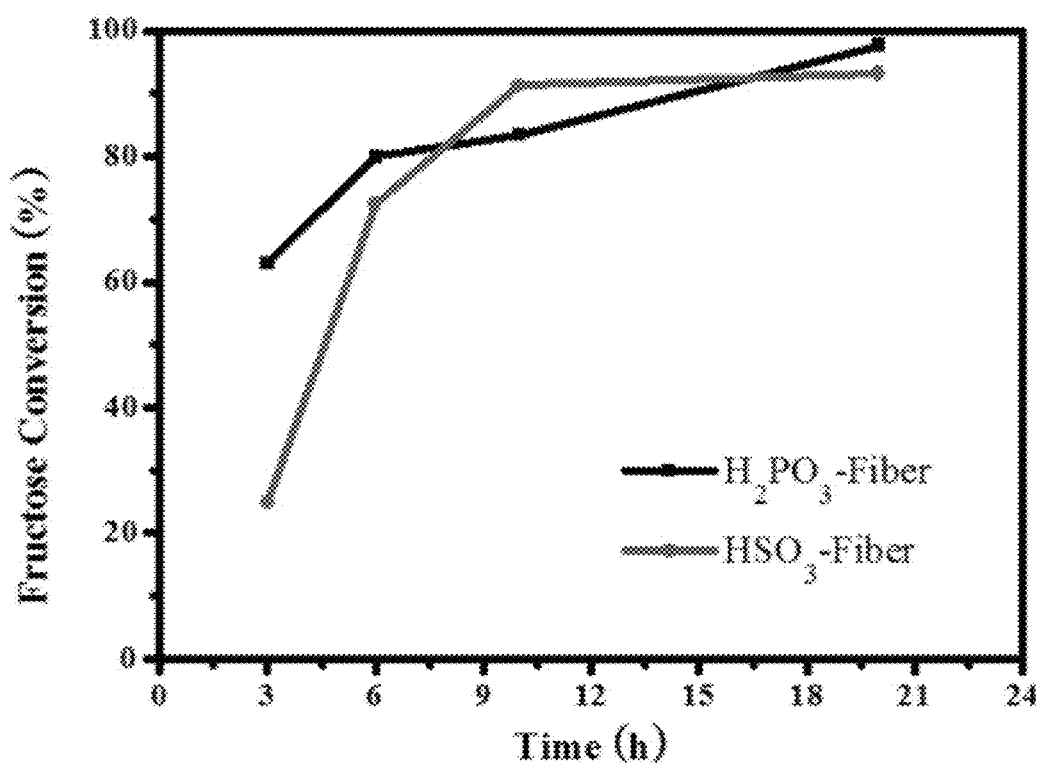

The effect of reaction time on the performance of the polymer catalysts was also investigated. FIG. 4A is a plot showing the progress of the fructose dehydration reaction over time (plot of HMF yield as a function of time) and FIG. 4B is a plot showing fructose conversion as a function of time.

As shown, the polymer catalysts grafted in vinyl sulfonic acid or vinyl phosphonic acid both reached 80% conversion of fructose in the first 6 hours at 120° C. and then slowly climbed to almost a 100% conversion over the next 18 hours. Further shown is that both co-polymer grafted fibers reached the highest yield for HMF in the first 6 hours and then leveled off and maintained the yield for the next 18 hours, with an indication that a further increase in reaction time would result in a decrease in selectivity. The decrease in the HMF selectivity is most likely due to its slow decomposition and formation of coke and humus, as indicated by the dark color of the reaction solution. For this reason, a reaction time of 6 hours and a temperature of 120° C. were selected as standard reaction conditions for recyclability tests.

Figure 4C:
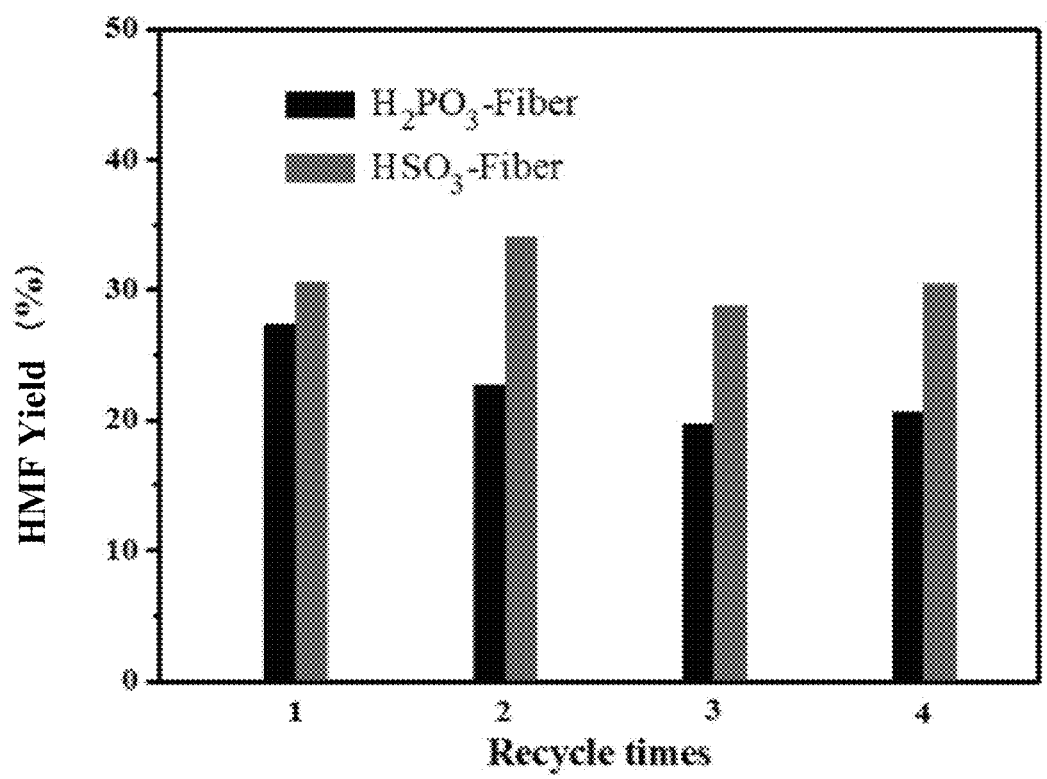

In order for a heterogeneous catalyst to be industrially relevant, it should maintain a high activity and selectivity over several reaction cycles in order to reduce cost and time. Thus, the above-described co-polymer grafted PE fibers were evaluated through four repeated reactions, as shown in FIG. 4C. The results in FIG. 4C show that both the vinyl sulfonic acid and vinyl phosphonic acid grafted fiber catalysts exhibited excellent stability for fructose conversion into HMF. In particular, after being used four times at 120° C. for 6 hours, the HMF yields for $HSO_3$-fiber and $H_2PO_3$-fiber maintained about 30% and 21% yields, respectively. Moreover, elemental analysis of a freshly grafted vinyl sulfonic or vinyl phosphonic co-polymer catalyst compared to a used catalyst after undergoing four reaction cycles shows that there was negligible loss in sulfur and phosphorus, thus further indicating a good stability.

The unique organic polymer grafted chains described herein contain randomly placed Brønsted acid sites, which swell to a great extent in water, but are not homogeneously distributed through the reaction mixture. The reaction mixture has several phases primarily as a result of the polymer fiber being a porous material and containing grafted co-polymer chains growing off the fiber and throughout the bulk of the fiber where interfacial regions exist. Moreover, the polymer chains grafted on the fiber surface (FIG. 2) can infinitely swell and increase with the organic acid sites on the polymer. Since most of the hydrophilic portion has a high interaction with water, the acid groups get maximum contact with the fructose, and the surface carboxylic acid and sulfonic or phosphonic acid groups work in synergy to form HMF in high yield and high conversion rate.

Adsorption experiments, analyzed by HPLC, were also conducted to study the affinity of the catalyst's microenvironment to both the substrate and the product. As evidenced by the results (Table 1), the adsorption of fructose is much higher than that of HMF on the polymer catalyst, thus indicating a higher affinity of the fructose towards the organic microenvironment of the catalyst. For this reason, the presence of diverse organic acid groups on fibers can enhance the adsorption of fructose and at the same time not have a large drawing force for HMF, thereby permitting the desorption of the HMF product without further dehydration.

While there have been shown and described what are at present considered the preferred embodiments of the invention, those skilled in the art may make various changes and modifications which remain within the scope of the invention defined by the appended claims.

What is claimed is:

1. A method for conducting an acid-promoted chemical reaction, the method comprising contacting an acid-reactive organic precursor in liquid form with a solid heterogeneous acid catalyst comprising a polyolefin structure of a macroscopic size of at least 1 micron in at least one dimension, wherein surfaces of the polyolefin structure have carboxylic acid groups and either sulfonic acid or phosphonic acid groups appended thereto, wherein the solid heterogeneous acid catalyst possesses an acid density of at least 6 mmol $H^+/g$, and wherein said acid-promoted chemical reaction is selected from dehydration, esterification, etherification, aldol condensation, enolization, oxidation, dehydrogenation, acetalization, and alkene hydration reactions, and wherein said solid heterogeneous acid catalyst is re-used in a subsequent acid-promoted chemical reaction.

2. The method of claim 1, wherein said polyolefin structure is selected from the group consisting of polyethylene, polypropylene, halogenated polyolefins, polystyrene, copolymers thereof, and mixtures thereof.

3. The method of claim 1, wherein said solid heterogeneous acid catalyst is in the form of fibers.

4. The method of claim 1, wherein said solid heterogeneous acid catalyst is in the form of a mesh, foam, sponge, or fabric.

5. The method of claim 1, wherein said solid heterogeneous acid catalyst comprises a plurality of acid-functionalized polyolefin macroscopic objects of at least 1 micron in one dimension.

6. The method of claim 1, wherein said solid heterogeneous acid catalyst comprises a single acid-functionalized polyolefin macroscopic object of at least 1 mm in one dimension.

7. The method of claim 1, wherein, following completion of said acid-promoted chemical reaction, said solid heterogeneous acid catalyst is separated from the acid-reactive organic precursor by a process not requiring filtration.

8. The method of claim 1, wherein grafts containing said carboxylic acid and sulfonic acid or phosphonic acid groups are appended to said surfaces of said polyolefin structure of macroscopic size, wherein said grafts have the formula:

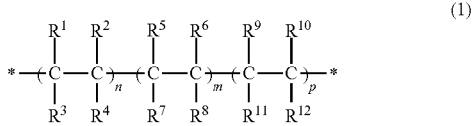

(1)

wherein $R^1$, $R^2$, $R^3$, $R^4$, $R^5$, $R^6$, $R^7$, $R^8$, $R^9$, $R^{10}$, $R^{11}$, and $R^{12}$ are independently selected from hydrogen atom; hydrocarbon groups R having at least 1 and up to 6 carbon atoms; acid groups selected from sulfonic acid groups, phosphonic acid groups, and carboxylic acid groups; acid precursor groups; halide atoms; and non-acid hydrophilic groups; wherein said hydrocarbon group R is unsubstituted or substituted with one or more heteroatom linkers and/or one or more heteroatom-containing groups comprising at least one heteroatom selected from nitrogen, oxygen, sulfur, and phosphorus; and the subscripts n, m, and p are independently selected from 0 or an integer of at least 1, provided that the sum of n, m, and p is an integer of at least 2;

provided that at least one of $R^1$, $R^2$, $R^3$, $R^4$, $R^5$, $R^6$, $R^7$, $R^8$, $R^9$, $R^{10}$, $R^{11}$, and $R^{12}$ is a sulfonic acid or phosphonic acid group, and at least one of $R^1$, $R^2$, $R^3$, $R^4$, $R^5$, $R^6$, $R^7$, $R^8$, $R^9$, $R^{10}$, $R^{11}$, and $R^{12}$ is a carboxylic acid group, and wherein the one of the bonds ending in an asterisk in the grafts depicted in Formula (1) is attached to the surface of said polyolefin structure of macroscopic size, and one of the bonds ending in an asterisk is attached to a terminating group selected from any of the groups provided above for groups $R^1$, $R^2$, $R^3$, $R^4$, $R^5$, $R^6$, $R^7$, $R^8$, $R^9$, $R^{10}$, $R^{11}$, and $R^{12}$.

9. The method of claim 1, wherein said acid-reactive organic precursor is within a polar solvent.

10. The method of claim 9, wherein said polar solvent is selected from water and water-soluble organic solvents.

11. The method of claim 9, wherein said polar solvent is water in the absence of an organic solvent.

12. The method of claim 1, wherein said acid-promoted chemical reaction is a dehydration reaction.

13. The method of claim 12, wherein said dehydration reaction converts a hexose into a furfural derivative.

14. The method of claim 13, wherein said hexose comprises fructose.

15. The method of claim 13, wherein said furfural derivative is 5-hydroxymethylfurfural.

16. The method of claim 13, wherein said dehydration reaction is conducted in water as the polar solvent in the absence of an organic solvent.

17. The method of claim 15, wherein said 5-hydroxymethylfurfural is produced in a yield of at least 20%.

18. The method of claim 15, wherein said 5-hydroxymethylfurfural is produced with a selectivity of at least 25%.

19. The method of claim 15, wherein said 5-hydroxymethylfurfural is produced in a yield of at least 20% with a selectivity of at least 25%.

20. The method of claim 13, wherein said hexose is derived from biomass.

* * * * *